United States Patent

Abul-Haj et al.

Patent Number: 5,348,706
Date of Patent: Sep. 20, 1994

[54] CALIBRATION SYSTEM AND METHOD FOR MAKING

[75] Inventors: Roxanne E. Abul-Haj, El Toro; Jacob J. Norman, Huntington Beach, both of Calif.

[73] Assignee: Minnesota Mining and Manufacturing Company, St. Paul, Minn.

[21] Appl. No.: 67,422

[22] Filed: May 24, 1993

Related U.S. Application Data

[60] Continuation-in-part of Ser. No. 849,753, Mar. 12, 1992, Pat. No. 5,278,072, which is a continuation-in-part of Ser. No. 747,533, Aug. 20, 1991, Pat. No. 5,171,029, which is a division of Ser. No. 514,704, Apr. 26, 1990, Pat. No. 5,057,278.

[51] Int. Cl.$^5$ ............................................. G01N 21/00
[52] U.S. Cl. ..................................... 422/100; 422/81; 422/103; 436/8; 128/DIG. 12
[58] Field of Search ............... 422/68.1, 81, 102, 100, 422/103; 436/8, 11; 128/DIG. 13, DIG. 12; 604/65, 67, 151

[56] References Cited

U.S. PATENT DOCUMENTS

| | | |
|---|---|---|
| 2,002,862 | 5/1935 | Moran . |
| 2,403,572 | 7/1946 | Wittenberg . |
| 2,503,376 | 4/1950 | Burgess . |
| 2,579,203 | 12/1951 | Putney . |
| 2,585,440 | 2/1952 | Collins . |
| 2,628,825 | 2/1953 | Kantor et al. . |
| 3,334,657 | 8/1967 | Smith et al. . |
| 3,658,445 | 4/1972 | Pulman et al. .................... 417/474 |
| 3,874,850 | 4/1975 | Sorensen et al. . |
| 3,884,640 | 5/1975 | Lock et al. . |
| 4,119,406 | 10/1978 | Clemens . |
| 4,266,941 | 5/1981 | Sullivan . |
| 4,285,703 | 8/1981 | Alexander . |
| 4,380,236 | 4/1983 | Norton .................................. 604/151 |
| 4,401,547 | 8/1983 | Schinkmann et al. . |
| 4,424,276 | 1/1984 | Clark et al. . |
| 4,443,407 | 4/1984 | Weinberg et al. . |
| 4,445,826 | 5/1984 | Tarr ....................................... 417/476 |
| 4,516,580 | 5/1985 | Polanyi . |
| 4,537,561 | 8/1985 | Xanthopoulos . |
| 4,540,351 | 9/1985 | Olson .................................... 417/476 |
| 4,559,040 | 12/1985 | Horres et al. . |
| 4,573,884 | 3/1986 | Troutner . |
| 4,604,263 | 8/1986 | Smernoff ............................... 422/50 |
| 4,635,467 | 1/1987 | Hoffa et al. ........................... 73/1 G |
| 4,640,820 | 2/1987 | Cooper ................................. 422/68 |
| 4,645,434 | 2/1987 | Bogen .................................. 417/476 |
| 4,668,634 | 5/1987 | Iwaski et al. ........................ 436/68 |
| 4,758,228 | 7/1988 | Williams ............................. 604/153 |
| 4,764,315 | 8/1988 | Brusa ................................ 261/140.1 |
| 4,798,590 | 1/1989 | O'Leary et al. .................... 604/153 |
| 4,830,013 | 5/1989 | Maxwell ............................. 128/637 |
| 4,844,871 | 7/1989 | Polaschegg ......................... 422/81 |
| 4,989,606 | 2/1991 | Gehrich et al. ..................... 128/637 |
| 5,057,278 | 10/1991 | Maxwell et al. ................... 422/81 |
| 5,074,756 | 12/1991 | Davis ................................... 417/45 |
| 5,094,820 | 3/1992 | Maxwell et al. ............... 422/82 R |
| 5,171,029 | 12/1992 | Maxwell et al. .............. 277/212 R |
| 5,278,072 | 1/1994 | Wall et al. ............................ 436/8 |

FOREIGN PATENT DOCUMENTS

| | | | |
|---|---|---|---|
| 0470818A3 | 12/1992 | European Pat. Off. ... | G01N 27/416 |
| 1489147 | 7/1967 | France . | |
| 58-150421A | 9/1983 | Japan ............................. | B01F 5/00 |
| WO92/18832 | 10/1992 | PCT Int'l Appl. .......... | G01D 18/00 |

OTHER PUBLICATIONS

European Search Report.
Souknanou et al., Webster's II New Riverside University Dictionary; 1984, p. 341.

Primary Examiner—Lyle A. Alexander
Attorney, Agent, or Firm—Gary L. Griswold; Walter N. Kirn; Dale E. Hulse

[57] ABSTRACT

An endless loop calibration system comprising a sensor cassette having a flow-through passage and at least one sensor to be calibrated, a chamber coupled to the sensor cassette to define an endless loop, a calibration liquid in the endless loop, and a valve element which is employed to prevent the flow of calibration liquid through the endless loop. This valve element, preferably carried by a housing, urges a tube compressor to squeeze a compressible tube against a curved wall surface sufficiently to prevent fluid from flowing in the compressible tube across the zone, and to maintain the at least one sensor in the sensor cassette wet with calibration liquid for long term storage of the calibration system.

11 Claims, 3 Drawing Sheets

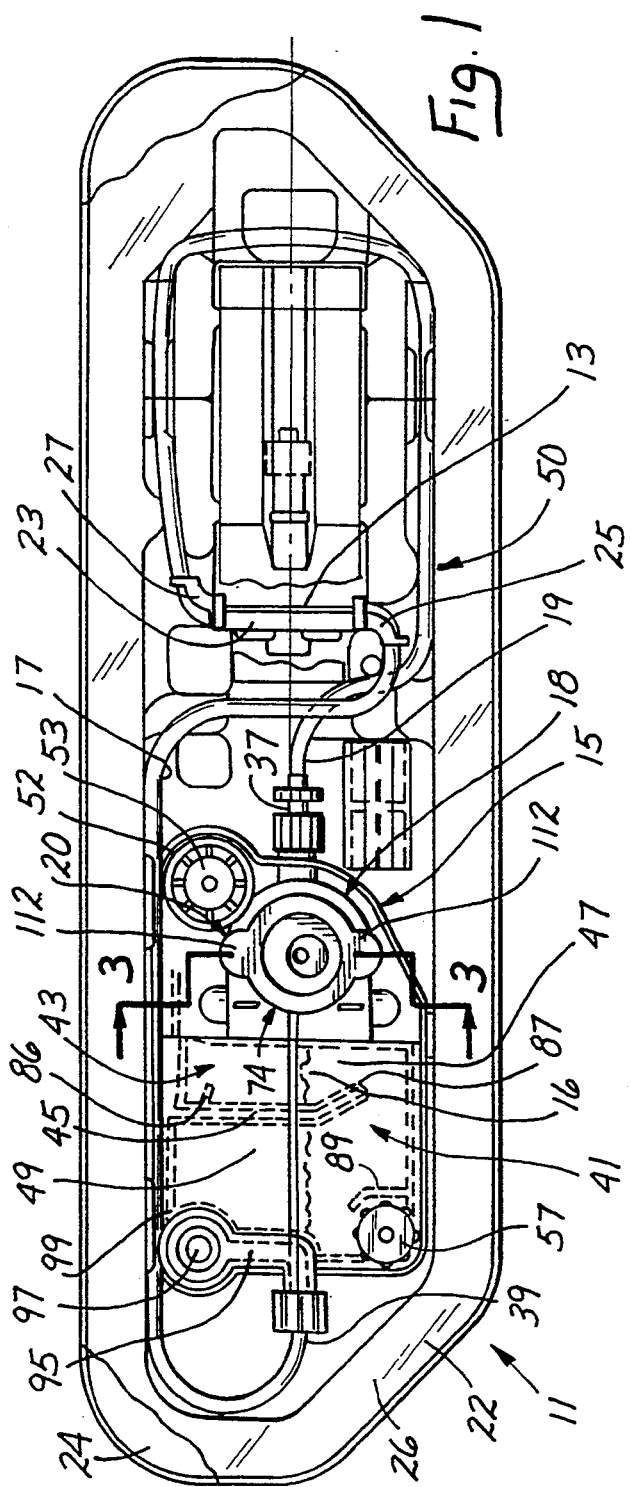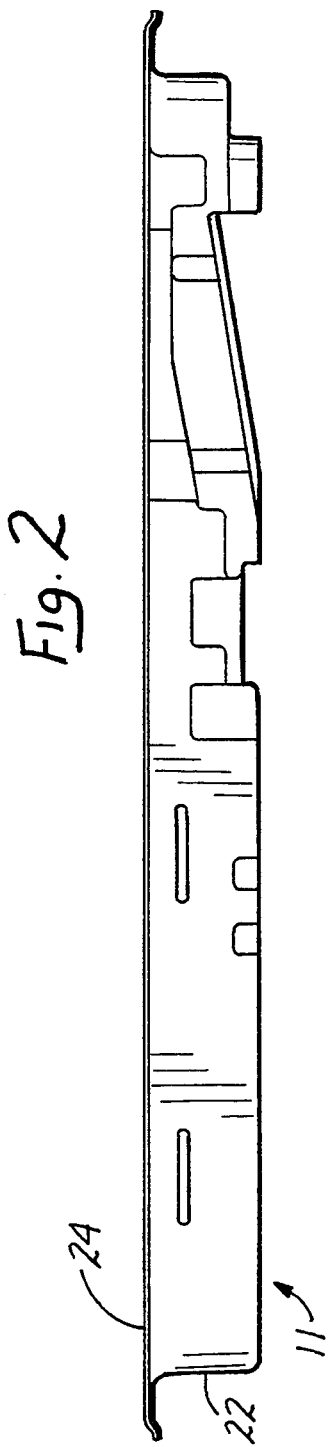

CALIBRATION SYSTEM AND METHOD FOR MAKING

RELATED APPLICATIONS

The present application is a continuation-in-part of Ser. No. 849,753 filed Mar. 12, 1992 now U.S. Pat. No. 5,278,072 which is incorporated in its entirety by reference herein. Application Ser. No. 849,753 filed Mar. 12, 1992 (now U.S. Pat. No. 5,278,072) in turn is a continuation-in-part of application Ser. No. 747,533, filed Aug. 20, 1991 (now U.S. Pat. No. 5,171,029); which application is a divisional of application Ser. No. 514,704, filed Apr. 26, 1990 (now U.S. Pat. No. 5,057,278).

BACKGROUND OF THE INVENTION

The present invention relates to calibration systems, to methods for producing such systems and to valve elements useful in such systems. More particularly, the invention relates to calibration systems for sensors, such as blood sensors, to methods for producing such systems so as to provide for effective sensor calibration and performance even after long term storage and to valve elements which are important components of such systems.

It is often necessary or desirable to monitor various parameters of blood and to obtain quantitative data concerning such parameters in real time. In order to accomplish this, blood is caused to flow through a flow-through housing past sensors which provide signals representative of the parameters of interest. For example, Cooper U.S. Pat. No. 4,640,820 shows a flow-through housing with fluorescent sensors which respond to the partial pressure of oxygen, the partial pressure of carbon dioxide and the pH of blood which has passed through the flow-through housing.

Prior to using the flow-through housing, the sensors must be calibrated. One calibration technique, which is used for the sensors of the Cooper patent, is to attach the sensor carrier to a calibration housing containing calibration liquid. This places the sensors in communication with a relatively large cross-sectional area passage. The gas or gases of interest are then bubbled through the calibration liquid. A similar technique is utilized to calibrate the sensors shown in Maxwell U.S. Pat. No. 4,830,013.

For some applications, it is desirable to utilize a flow-through housing having a relatively small cross-sectional area and to maintain that area sterile during calibration. In fact, the cross-section area is sufficiently small so that, when gas is passed through the liquid, the surface tension may cause the calibration liquid to be expelled from the passage and prevent exposure of the sensors to the gases in the calibration liquid and thus cause an inaccurate calibration.

Maxwell et al U.S. Pat. No. 5,057,278 discloses a very useful sensor calibration system for sensors associated with flow-through cassettes. The disclosure of this patent is incorporated in its entirety herein by reference.

It is beneficial that sensors in such flow-through cassettes be maintained wet with calibration liquid during storage, even during storage for periods of months or even up to about one year. Since it is not desirable to fill the entire flow-through or endless loop of the calibration system with calibration liquid, for example, because such large amount of calibration liquid can unduly increase the amount of time required to effectively calibrate the sensors, the calibration system should be manufactured and maintained so that a limited amount of the calibration liquid is used and effectively wets the sensors.

Prior art systems have effectively maintained the sensors wet with calibration liquid by stopping the flow of calibration liquid through the endless loop. This has been done, for example, by providing an elongate section of tubing in the endless loop. The elongate section of tubing is sharply kinked during packaging and a retainer or clamp is secured to the tubing to maintain the tubing completely occluded. Further, the interior of the tubing is coated with a material, such as a polyxylene, which prevents the kink in the tubing from becoming permanent. When the calibration system is ready for use, the clamp is removed from the tubing and the tubing is unkinked, thus allowing calibration liquid to be pumped through the endless loop.

Although the kinked tube and clamp effectively provide that the sensors remain wet with calibration liquid during storage, this approach does have certain disadvantages. For example, the long length of tubing adds to the volume of the endless loop and is an additional component of the calibration system which must be assembled. In addition, the retainer or clamp must be removed before use, which removal is an additional step and may require a special removal tool. Further, there is some chance of damaging the tubing in removing the retainer or clamp, which is fastened directly on the tubing.

It would be advantageous to provide a new calibration system for maintaining such flow-through cassette sensors wet with calibration liquid during storage.

SUMMARY OF THE INVENTION

New calibration systems, methods for producing calibration systems and valve elements useful in such calibration systems have been discovered. The present calibration systems very simply and effectively provide an endless loop in which calibration liquid is maintained so as to wet the sensor or sensors in the loop during prolonged periods of storage. No kinking and direct clamping of long lengths of tubing is required so that the disadvantages of the prior art, noted above, are avoided. A relatively short length of compressible tubing is occluded in response to the presence of a valve element in a peristaltic pump mechanism to prevent calibration liquid flow through the endless loop and maintain the sensor or sensors wet with the calibration liquid. The valve element does not come in direct contact with the occluded tubing. Thus, when the valve element is removed, which can be easily accomplished, there is very little, if any, chance of damaging the occluded tubing. The present calibration systems, which are often disposable, have fewer components than prior art systems. This, together with a relatively simple and straightforward design, reduces costs.

The valve elements of the present invention are straightforward in construction. They are conveniently placed relative to, and are preferably carried by, a housing so as to perform the tube occluding function. In one embodiment, the valve element can hie conveniently structured to be coupled with a motor and drive mechanism to move a tube compressor, and thereby pump calibration liquid through the loop during sensor calibration service.

In one broad aspect of the present invention, an apparatus is provided which comprises a housing, a curved wall surface on the housing, a tube compressor and a valve element. The housing has an inlet, an outlet and a passage. The compressible tube, carried by the housing, defines at least a portion of the passage. This tube is located between the curved wall surface and the tube compressor and is wrapped in a circumferential direction at least partly around the tube compressor. The tube compressor, in turn, is mounted on the housing for movement relative to the curved wall surface to squeeze a region of the compressible tube which moves along the compressible tube to thereby pump fluid, for example, calibration liquid. The valve element, preferably carried by the housing, urges the tube compressor to squeeze a zone of the compressible tube sufficiently to prevent fluid, calibration liquid, from flowing through the tube across the zone. With the valve element performing this urging function, flow of calibration liquid is effectively prevented and the sensor or sensors in fluid communication with the compressible tubing can be effectively maintained wet with the calibration liquid during long term storage.

In one embodiment, the apparatus further comprises a package base and a package cover attached to the package base. The package base and package cover together define an enclosed space in which the housing and the valve element, and preferably a sensor cassette with a flow-through passage and at least one sensor to be calibrated, are located.

In another broad aspect of the invention, methods for producing a calibration system are provided. These methods comprise forming a system comprising a sensor cassette having a flow-through passage and including at least one sensor to be calibrated, means defining a chamber, and a housing defining a fluid passage so that the flow-through passage, chamber and fluid passage are parts of an endless loop, preferably a closed, endless loop. The housing may be, and preferably is, as described above. A calibration liquid is introduced into the endless loop, preferably positioned to wet the sensor or sensors in the sensor cassette. A valve element, such as described above, is placed relative to the housing to urge the tube compressor to squeeze the tube sufficiently to prevent calibration liquid from flowing through the endless loop.

In a preferred embodiment, the system includes a package base made of polymeric material which is air, water and microorganism impermeable and is able to withstand autoclave sterilization conditions. Further, a package cover is attached to the package base to thereby form an enclosed package defining an interior space in which the remainder of the system is located. The package cover is made of a polymeric material which is air and water permeable, microorganism impermeable and is able to withstand autoclave sterilization conditions. Thereafter, the enclosed package is subjected to effective autoclave sterilization conditions to thereby sterilize at least a portion of the system, for example, the components of the system located in the interior space defined by the package base and package cover. The use of such polymeric packaging materials, together with the present valve elements, allows for the relatively easy and cost effective production of calibration systems which are effectively sterile and in which the sensor or sensors are maintained wet with calibration liquid. Thus, such calibration systems are safe and effective in use even after being stored for periods ranging up to about one year or longer.

The valve elements useful in the above-noted apparatus, calibration systems and methods, comprise a top portion having a top surface, a bottom surface and central axis passing through the planes defined by both of these surfaces. The top portion is adapted to contact the housing, described herein, to facilitate positioning the valve element relative to the housing. An intermediate portion, joined to the top portion, is provided and includes a sidewall, a lower surface and central axis generally parallel to the sidewall. This sidewall extends from the bottom surface of the top portion to the lower surface. The central axis of the intermediate portion is different from the central axis of the top portion. The sidewall of the intermediate portion is adapted to urge the tube compressor, described herein, to a desired position, for example, to prevent fluid flow through the endless loop. A bottom portion is joined to the intermediate portion and includes a sidewall, a bottom end surface and a central axis generally parallel to this sidewall. The central axis of this bottom portion is the same as the central axis of the top portion. At Least a portion of the sidewall of the bottom portion is adapted to contact the housing to facilitate positioning the valve element relative to the housing.

The invention, together with additional features and advantages thereof, may best be understood by reference to the following description taken in connection with the accompanying illustrative drawings.

BRIEF DESCRIPTION OF THE DRAWINGS

FIG. 1 is a top plan view illustration of a packaged sterile-loop calibration system constructed in accordance with the teachings of this invention, with the package cover being broken away for illustrative clarity.

FIG. 2 is a side plan view of the packaged sterile-loop calibration system shown in FIG. 1.

DESCRIPTION OF THE PREFERRED EMBODIMENT

Figure 3:
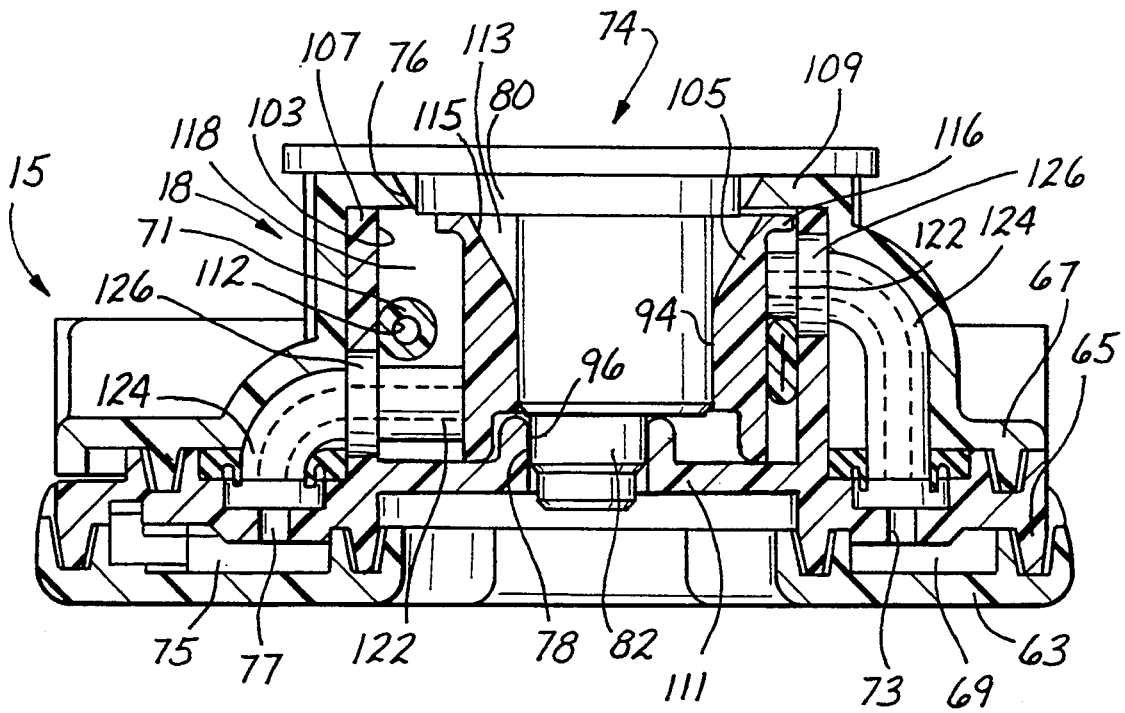
FIG. 3 is an enlarged sectional view taken generally along line 3—3 of FIG. 1. For the sake of clarity, the valve element is not shown in section.

FIG. 1 shows a sterile-loop calibration system 11 which generally comprises a sensor device or cassette 13, a calibration cuvette 15 including a housing 18, sterile calibration liquid 16, conduit means, including conduits 17 and 19, for coupling the calibration cuvette to the sensor cassette, valve element 74 which is carried by the housing, package base 22 and package cover 24. The sterile-loop calibration system 11 shown in FIG. 1 is a disposable component or apparatus and is designed for use with the calibration apparatus 21 (FIG. 5), which is a reusable component.

The sensor cassette 13 may be of the type shown in Gehrich et al U.S. Pat. No. 4,989,606 which is incorporated in its entirety herein by reference. Briefly however, the sensor cassette 13 includes a flow-through passage 23 having first and second ends in the form of tube fittings 25 and 27 which are joined to the conduits 17 and 19, respectively. Three sensors (not specifically shown), to be calibrated, are carried by the sensor cassette 13 in communication with the flow-through passage 23. The sensors may be, for example, for sensing carbon dioxide, pH and oxygen. The flow-through passage 23 has a very small cross-sectional area and may be, for example, rectangular and have dimensions of about 0.15 inch×0.164 inch.

The calibration cuvette 15 has an inlet 37, an outlet 39 and a cuvette passage 41 extending through the cuvette from the inlet to the outlet. The cuvette passage 41 includes a chamber 43 which is divided by a weir 45 or divider into a sparging chamber section 47 and a settling chamber section 49.

The flow-through passage 23, the conduits 17 and 19, and the cuvette passage 41 form a sterile loop 50 which provides an endless loop in which the sterile calibration liquid 16 can be circulated.

The cuvette 15 has a gas injection passage leading from a gas injection port 52 to a location in the cuvette passage 41 for injecting gas into the cuvette passage and means in the form of a threaded closure cap 53 for closing the gas-injection port. The cuvette 15 also includes a gas vent, such as a restricted orifice, for example, having a diameter of about 1/16 inch. The gas vent leads from the settling chamber 49 to the exterior of the cuvette. The gas vent may be completely closed by a closure cap 57.

The construction of the cuvette 15 can best be understood by reference to FIGS. 1 and 3. Although various constructions are possible, as shown in FIG. 3, the cuvette 15 includes a housing 18 of multiple molded plastic components, such as a base 63, a cover 65 and a top section 67. At least the cover 65 and the top section 67 are preferably transparent. The base 63, the cower 65 and the top section 67 may be suitably coupled together as with an adhesive.

As shown in FIG. 3, the inlet 37 leads to an inlet passage section 69 of the cuvette passage 41. A radially compressible tube 71 communicates with the inlet passage section 69 through an aperture or opening 73 in the cover section 65 and with a chamber inlet section 75 through an aperture of opening 77 which also is in the cover 65 . The chamber inlet section 75 leads to the sparging chamber 47.

The gas injection passage is defined in part by an externally threaded tube affixed to the top section 67. A gas-sterilizing filter is supported on the cover 65 and is retained in place by a spider section of the top section 67. The gas-sterilizing filter 81 may be, for example, a 0.2 micron pore filter which is capable of sterilizing gas which passes through it due to the small pore size. Accordingly, with the cap 53 removed, a non-sterile gas can be introduced as described below to the injection port 52 whereby it will pass through the filter an aperture in the cover 65, and a passage section of the gas injection passage between the base 63 and the cover 65 to the chamber inlet section 75. For example, the gas injected into the gas injection passage may comprise $CO_2$, $O_2$ and an inert gas, such as nitrogen.

With this construction, the sterile calibration liquid 16, with the gas therein, is introduced into the sparging chamber 47. Premixing of the gas and liquid occurs in chamber inlet section 75. As shown in FIG. 1, the base 63 preferably has a baffle 86 adjacent the weir 45 and above the location where the chamber inlet section 75 opens into the sparging chamber 47 for the purpose of breaking up larger bubbles that may exist in the liquid. The sparging chamber 47 provides time for the gas to equilibrate in the calibration liquid 16, and as liquid fills the sparging chamber, it is allowed to flow over the free end 87 of the weir 45 and fall into the settling chamber 49. As gas bubbles through the calibration liquid 16 in the sparging chamber 47, foam is generated and also flows over the weir 45 into the settling chamber 49. In the settling chamber 49, any remaining gas bubbles are given another opportunity to rise to the top and be vented through the vent 55, which is in the form of an aperture in the cover 65. A baffle 89 may be provided adjacent the vent 55 to reduce the likelihood that the liquid component of any foam will exit through the vent 55.

As shown in FIG. 1, the cuvette passage 41 also includes an outlet passage section 95 leading from the settling chamber 49 to the outlet 39. The cuvette 15 has a temperature sensing location which, in this embodiment, is in the form of a temperature well 97 adapted to receive a temperature probe in heat exchange relationship with the outlet passage section 95. Although various constructions are possible, the outlet passage section 95 may communicate with the settling chamber 49 through an aperture 99 as shown in FIG. 2. The aperture 99 is positioned to force flow to occur around the temperature well 97.

In order to move the calibration liquid 16 through the sterile loop 50, it is necessary to provide a pump to force the calibration liquid through the sterile loop. The pump includes pump components in the cuvette 15 and an external rotary input or rotary driving element 101 (FIG. 5) which is part of the calibration apparatus 21. The pump components in the cuvette 15 include a curved wall surface 103 (FIG. 3), the compressible tube 71 and a tube compressor 105. The opposite ends of the tube 71 form an inlet and an outlet, respectively, for the pump.

More particularly, the wall surface 103 in this embodiment is cylindrical and constitutes the inner surface of a cylindrical boss 107, portions of which are formed integrally with the cover 65 and the top section 67. The tube compressor 105 is surrounded by the wall surface 103, and the tube 71 is wrapped in a circumferential direction about one time around the tube compressor and lies between the tube compressor and the wall surface 103.

The cover 65 and the top section 67 have flanges 109 and 111, respectively, which provide retaining surfaces for restraining the tube compressor 105 against axial movement relative to the wall surface 103. Because there is a radial clearance between the tube compressor 105 and the wall surface 103 and because the flanges 109 and 111 do not restrain the tube compressor against radial movement, the tube compressor is mounted on the housing for free radial movement relative to the wall surface 103 and the boss 107. In other words, the tube compressor 105 can be moved radially in a direction from the centered or neutral position, with the only consequence being the squeezing of the compressible tube 71. With this construction, the tube compressor 105 can be caused, by the action of rotary input 101, to roll along the tube 71 to squeeze the tube in a zone or region which moves along the tube to thereby pump fluid in the tube. In the neutral position, the tube 71 is not squeezed.

The tube compressor 105 is generally cylindrical and tubular and has an outwardly opening passage or cavity 113 having a mouth 115 which is flared radially outwardly to receive the rotary input 101 as described hereinbelow. Thus, the cavity 113 provides means on the tube compressor 105 for use in releasably drivingly coupling the tube compressor to the external rotary input 101 whereby the tube compressor can be rolled along the tube 71 to pump fluid in the tube. The tube compressor 105 is constructed of a suitable rigid material, such as a rigid plastic, and the cavity 113 is defined by a smooth, hard, low-friction surface which surface is smoother, harder and of substantially lower friction than the tube 71. This facilitates reception of the rotary driving element 101, which is also smooth and hard and provides a low-friction surface.

The tube compressor 105 also has an annular flange 116 at the opening of the mouth 115. The flange 116 cooperates with the flange 109 to close the upper end of a compartment 118 between the tube compressor 105 and the wall surface 103 so that the tube 71 cannot escape out the upper end of the compartment regardless of the radial position of the tube compressor 105.

The tube 71 has opposite end portions having regions 122 which extend generally tangentially of the tube compressor 105 and regions 124 which extend axially of the tube compressor 105 to their respective ends. Each set of the regions 122 and 124 is integrally joined by a 90-degree bend portion. The tangential regions 122 have annular flanges 126 which are captured as shown in FIG. 3 by the boss 107 and adjacent regions of the top section 67 to thereby hold the tube 71 in position.

To prevent leakage of the sterile calibration fluid, it is important to seal the opposite ends of the tube 71 to the confronting portions of the cover 65.

As shown in FIGS. 1 and 3, a valve element 74 is positioned to prevent the flow of calibration liquid 16 through tube 71. Valve element 74 is carried by housing 18 and extends into cavity 113. Housing 18 includes top indexing surface 76 and bottom indexing surface 78 which come in contact with sidewall 80 and sidewall segment 82, respectively, of valve element 74 to properly position and locate the valve element with respect to the housing.

The valve element 74 is more fully described with reference to FIG. 4. Thus, valve element 74 includes top portion 84, an intermediate portion 86 and a bottom portion 88. The central axis 90 of top portion 84 is the same as the central axis of the bottom portion 88. The intermediate portion 86 is eccentric to both the top portion 84 and the bottom portion 88. That is, the central axis 92 of intermediate portion 86 is different from the central axis 90 of top portion 84 and bottom portion 88. This eccentricity of intermediate portion 86 is sufficiently great so that, as shown in FIG. 3, when valve element 74 is positioned relative to housing 18 so that sidewall 94 of the valve element is in contact with the tube compressor 105, the tube compressor is urged to a position such that a zone of tube 71 is completely occluded. This occlusion of a zone of the tube prevents any flow of calibration liquid 16 through the tube, as well as through sterile loop 50.

Thus, with valve element 74 carried by housing 18 as shown in FIG. 3, the calibration liquid 16 is effectively prevented from flowing through the sterile loop 50.

Valve element 74 is constructed of a suitable rigid material, such as a rigid plastic and the sidewalls of the valve element are hard surfaces.

Figure 4:
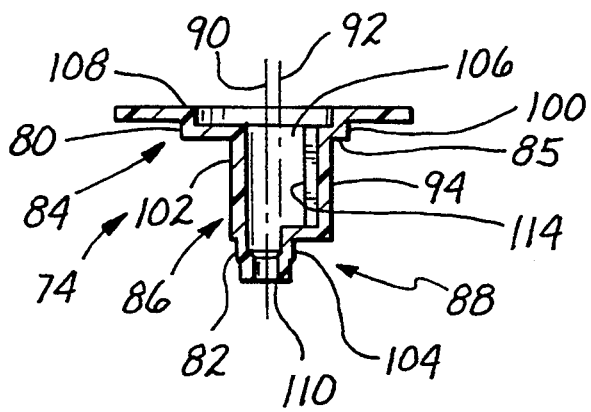
FIG. 4 is a sectional view of the valve element included in the system shown in FIG. 1.

As shown in FIG. 4, top portion 84 at sidewall 80 has a larger periphery 100 than the periphery 102 of sidewall 94 transverse to the central axis 92. In turn, periphery 102 is larger than the circular periphery 104 of the sidewall segment 82 of bottom portion 88 transverse to the axis 90. Although different constructions can be utilized, the embodiment shown in FIGS. 1, 3 and 4 includes an intermediate portion 86 which is in the form of a right circular cylinder. The bottom surface 85 of top portion 84 has a periphery 100 which is circular. Also, the bottom end surface 110 has a circular periphery. In addition, valve element 74 includes a open through space 106 which extends from the top surface 108 to the bottom end surface 110 of the valve element. In addition, as best shown in FIG. 1, top portion 84 includes oppositely disclosed finger tabs 112 which, with the valve element 74 being carried by housing 18, extend radially outwardly beyond the housing. These finger tabs 112 facilitate the engaging and disengaging of valve element 74 relative to housing 18.

A stiffening element 114 is secured to sidewall 94 of intermediate portion 86 and extends into space 106. Stiffening element 114, which extends generally parallel to central axis 92 across substantially the entire length of intermediate portion 86, acts to enhance the strength of valve element 74, and in particular of the intermediate portion. Valve element 74 can be formed in a single piece, for example, by conventional plastic molding techniques.

Since valve element 74 is designed to be placed in and carried by housing 18 to occlude compressible tube 71 for a long period of time, it is beneficial to construct the tube to withstand such long term occlusion. One particularly useful material of construction for compressible tube 71 is a silicone polymeric material. The interior walls 112 of tube 71 are preferably coated with a material which acts to inhibit such interior walls from fusing to one another or together during extended periods when the tube is totally occluded. Although various different materials can be used for the coating, very useful coating materials are those selected from the polyxylylenes and mixtures thereof. A particularly useful polyxylylene is that sold under the trademark Parylene C and available from Viking Technology, Inc. of San Jose, Calif.

Calibration system 11 is preferably produced as follows:

All of the components of system 11 are produced and coupled together, except for calibration liquid 16 and package base 22 and package cover 24. The cuvette 15 is then filled with a suitable amount of calibration liquid 16, for example, through one or more of the fluid ports, noted herein. All the fluid ports are then closed. The calibration liquid 16 is maneuvered in loop 50 so as to wet the sensors in sensor cassette 13. With the calibration liquid 16 wetting these sensors, valve element 74 is inserted into cavity 113, as shown in FIG. 3. This prevents the calibration liquid 16 from flowing through loop 50 and, in effect, ensures that the sensors in sensor cassette 13 are maintained wet with the calibration liquid. Alternately, the valve element 74 can be placed in cavity 113 prior to the calibration liquid 16 wetting the sensors in sensor cassette 13. By manually rotating the valve element 74, calibration liquid 16 can be made to flow in loop 50 until the calibration liquid suitably wets the sensors in sensor cassette 13. Once this wetting has occurred, and a suitable amount of calibration liquid 16 is present to maintain such wetness, the rotation of valve element 74 is stopped.

The cuvette 15 and loop 50 are placed in the package base 22, which is suitably configured to fixedly hold these components in place. Package cover 24 is then attached to package base 22 so that an enclosed space 26 is formed in which the other components of system 11 are located.

In one particularly useful embodiment, the package base is made of a polymeric material which is air, water and microorganism impermeable and is able to withstand autoclave sterilization conditions. The package cover is made of a polymeric material which is air and water permeable, microorganism impermeable and is able to withstand autoclave sterilization conditions. A very useful material of construction for the package base 22 is selected from polycarbonates and mixtures thereof. The package cover 24 is preferably made of a material selected from polyolefins, more preferably spun bonded polyolefins, and mixtures thereof. One very useful material of construction for the package cover 24 is a spun bonded polyolefin sold by Dupont under the trademark Tyvec.

With the calibration system packaged as shown in FIGS. 1 and 2, the package can then be subjected to conventional steam autoclave sterilization conditions to sterilize the system. Such conditions can include, for example, a temperature in the range of about 120° C. to about 170° C. for a time in the range of about 0.1 hours to about 3 hours or more in a steam medium. Being able to sterilize the packaged system, within the package, as described above, is very beneficial in that excellent maintenance of sterility is achieved. In addition, this method of producing the calibration system 11 reduces the number of processing steps involved. After sterilization, the packaged system 11 is placed in a sealed sterile barrier pouch, for example, made of commercially available metallized polymeric material, which is air, water and microorganism impermeable, and can be stored for a prolonged period of time with substantially no detrimental effects caused by such long storage period.

In an alternate embodiment, the cuvette 15, loom 50 (including calibration liquid 16) and coupled valve element 15 are sterilized, for example, by being subjected to effective steam autoclave sterilization conditions. This sterile combination of components is then placed in an enclosed package including a base and a cover both of which are made of materials which are air, water and microorganism impermeable. This packaged system can also be stored for a prolonged period of time with substantially no detrimental effects caused by such long storage period.

As shown in FIG. 1, the gas-injection port 52, the temperature well 97 and the tube compressor 105 all open at the exterior of the housing on the same side of the housing.

Figure 5:
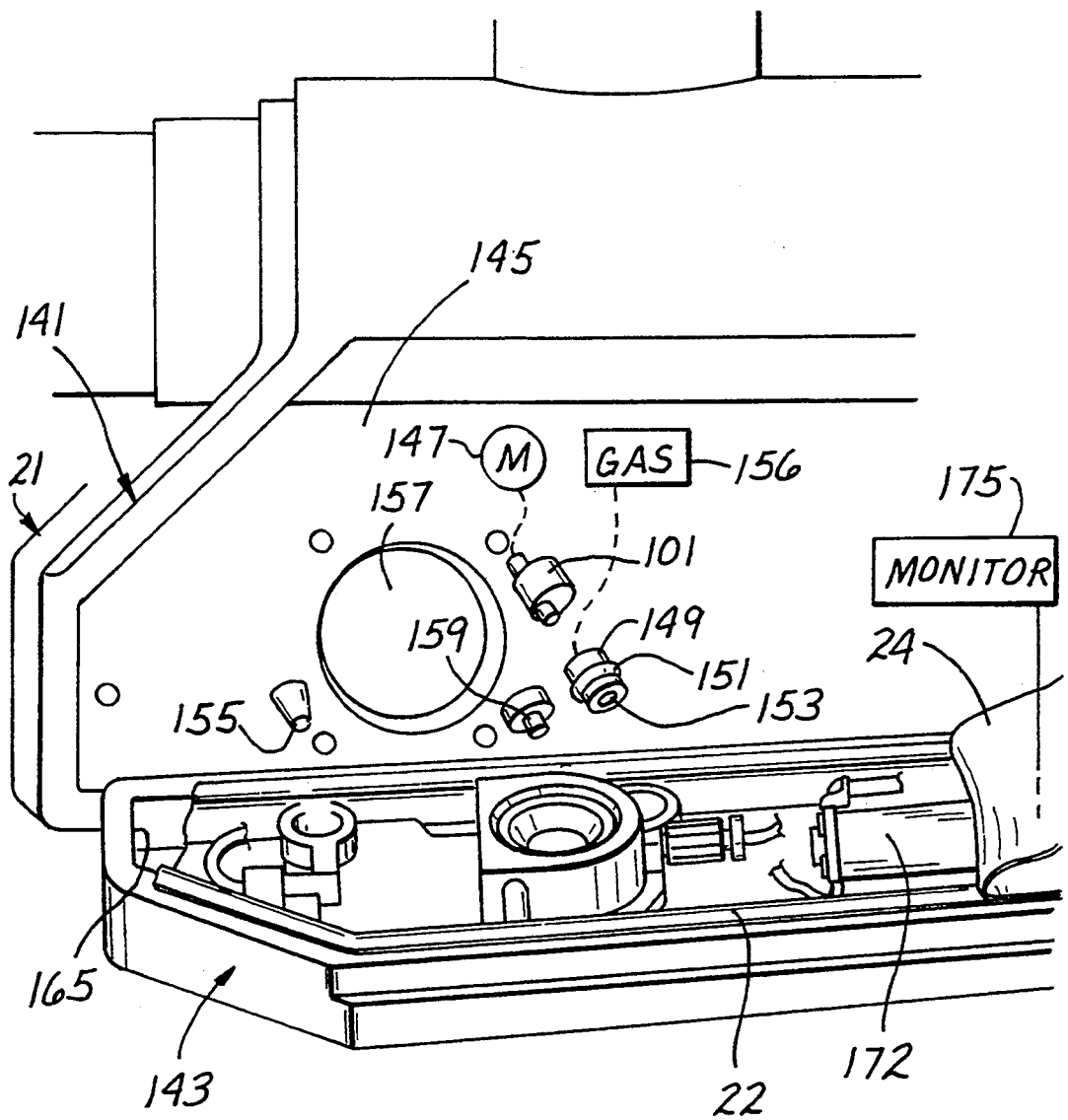
FIG. 5 is a fragmentary perspective view illustrating the calibration system and, in particular, the calibration apparatus, with the calibration system in a package base and the door of the calibration apparatus in the open position.

The calibration apparatus 21 includes a supporting structure 141 and a door 143 pivotally mounted on the supporting structure for movement between an open position shown in FIG. 5 and a closed position. The rotary driving element 101 is rotatably mounted on the supporting structure 141 and projects outwardly from a front surface 145 thereof. The rotary driving element 101 is an eccentrically mounted cam which is rotatable about an axis. In this embodiment, the rotary driving element 101 is driven by a suitable motor 147, which is also carried by the supporting structure 141. The rotary driving member 101 serves as a cam to move the tube compressor 105 to bring about a pumping action in the tube 71.

A tube 149 carrying an annular seal 151 and defining a gas exit port 153 is mounted on the supporting structure 141 and projects outwardly from the front surface 145 in the same direction as the rotary driving element 101. A temperature sensor in the form of a temperature probe 155 is also mounted on the supporting structure 141 and projects outwardly from the front surface 145 in the same direction as the rotary driving element 101. The tube 149 is coupled to a source 156 of calibration gas, which also may be carried by the supporting structure 141. The temperature probe 155 may be coupled to an appropriate temperature read out (not shown) and/or to a circuit for controlling a heat lamp 157 which is carried by the supporting structure 141 and faces outwardly from the front surface 145 in the same direction as the rotary driving element 101. The heat lamp 157 is provided for the purpose of maintaining the calibration liquid 16 at the desired temperature, such as 37° C.

A spring-biased ejector 159 is mounted on the supporting structure 141 and projects outwardly from the front surface 145. When the cuvette 15 is positioned on the supporting structure 141 as described below and the door is in the closed position, the ejector 159 applies a resilient force to the cuvette to urge the door toward the open position of FIG. 5.

The package cover 24 which can be peeled back as shown in FIG. 5 to expose the portions of the system 11 carried by the package base 22. The door 143 has a recess 165 for receiving the package base 22. The package base 22 and the recess 165 have sufficiently complementary configurations so that the recess can at least assist in releasably retaining the package base in a predetermined orientation. Similarly, the package base 22 has a sufficiently complimentary configuration to retain the cuvette 15 and loop 50 within the package base in a predetermined orientation.

In use to calibrate the sensors in sensor cassette 13, the package cover 24 is peeled back from the base 22, and the package base is placed in the recess 171 of the door 143 as shown in FIG. 5. An optical head 172 is coupled to the sensor cassette 13 in a known manner to optically couple the sensors to an instrument or monitor 175. The closure caps 53 and 57 are removed to expose the gas injection port 52 and the gas vent 55, respectively. Valve element 74 is removed from housing 18. The doer 143 is then pivoted from the open position of FIG. 5 to the closed position, and the door is retained in the closed position by a suitable lock.

Placing the door 143 in the closed position positions the cuvette on the supporting structure 141. When so positioned, the rotary driving element 101, the tube 149 and the temperature probe 155 are received in the cavity 113, the well 135 and the temperature well 97, respectively, and this results automatically from simply closing the door, i.e., moving the door to the closed position. In addition, the ejector 159 is resiliently compressed against a region of the cuvette 15 so that the ejector resiliently loads the door 143 toward the open position of FIG. 5.

The flared mouth 115 serves as a cam follower or leading as the rotary driving element 101 is inserted into the cavity 113. Specifically, the rotary driving element 101 cooperates with the flared mouth 115 to cam the tube compressor 105 radially to the position in which on side of the tube 71 is tightly squeezed between the tube compressor and the curved wall surface 103, and the other side of the tube 71 is uncompressed.

The rotary driving element 101 has a nose which is received in a bearing when the door is in the closed position.

Because the tube compressor 105 is free to move radially inside the curved wall surface 103, eccentric rotation of the rotary driving element 101 about the axis 146 (FIG. 9) cause the tube compressor 105 to roll along the tube to create a peristaltic pumping action to pump the calibration liquid 16 through the sterile loop 50 including the flow-through passage 23 of the cuvette 15. Because the surfaces defining the cavity 113 and the exterior of the rotary driving element 101 are relatively hard, smooth and of low friction, the insertion of the rotary driving element 101 into the cavity 113 is easily accomplished by simply closing the door 143 even though a camming action and consequent radial movement of the tube compressor 105 must occur.

It should be noted that no angular indexing of the rotary driving element 101 is necessary in order to insert the rotary driving element into the cavity 113 of the tube compressor 105. Thus, driving engagement can be established between the rotary driving element 101 and the tube compressor 105 automatically as a result of moving the door 143 to the closed position and regardless of the angular orientation of the rotary driving element 101.

The closing of the door 143 also inserts the tube 149 to place the gas exit port 153 in communication with the gas injection port 52. The gas is supplied at some positive pressure, and consequently, the pressure in the cuvette passage 41 is greater than ambient. For this reason, as vents from the gas vent 55, and the positive pressure existing in the cuvette passage 41 and the flow of gas outwardly inhibits inward flow of gas or liquid through the gas vent 55 into the cuvette passage 41. The gas is introduced into the stream of calibration liquid 16 being circulated by the pump and is premixed with the liquid for introduction into the sparging chamber 47. The gas is sterilized by the filter so that sterile gas is introduced into the sterile calibration liquid 16. Gas which vents from the vent 55 can escape from within the calibration apparatus 21.

In the closed position of the door 143, the temperature probe 155 is received within the well 97 so that temperature readings can be taken of the liquid in the outlet passage section 95. In addition, the heat lamp 157 is placed in close proximity with the cuvette 15 so that the calibration liquid 16 can be heated to the desired temperature.

When the partial pressures of the gases of interest reach the desired level in the calibration liquid 16, the monitor 175, is calibrated to the particular sensor cassette 13 and, particularly, the sensors thereof using conventional techniques. Thereafter, the lock is unlocked, and the door 143 is pivoted to the open position by the ejector 159 to remove the cuvette 15 from the calibration apparatus 21. The sensor cassette 13 can be employed with the monitor 175 for the measurement of the relevant blood parameters of interest of a patient as disclosed, for example, in Gehrich et al U.S. Pat. No. 4,989,606 referred to above.

Figure 6:
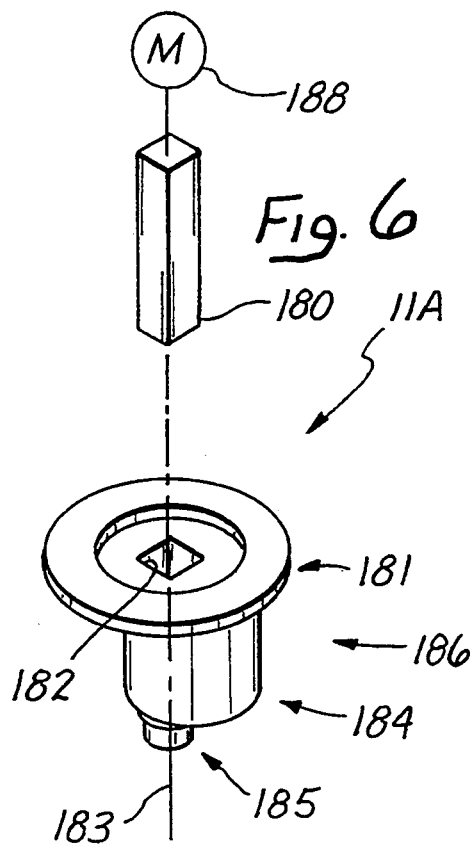
FIG. 6 is a schematic illustration of an alternate embodiment of the valve element being used as a pump driver.

FIG. 6 illustrates an alternate embodiment. Except as expressly stated herein, the system, identified as 11A, depicted in FIG. 6 is structured and performs the same functions as the system 11.

The primary differences between the system 11A and the system 11 is the presence of a square shaped drive shaft 180 in place of the rotary driving element 101, and the square shaped cavity 182 defined by the intermediate portion 184 of valve element 186. Square shaped cavity 182 has a square (non-circular) periphery transverse to the central axis of the intermediate portion 184. Square shaped cavity 182 has a central axis 183 which is the same as the central axis of both top portion 181 and bottom portion 185. The drive shaft 180 is operatively coupled to motor 188 and is configured to fit into the square shaped cavity 182.

The system 11A operates as follows. The valve element 186 is maintained in place in cavity 113 when the door 143 is moved to the closed position. Drive shaft 180 is positioned so that as door 143 is closed, the drive shaft is introduced into the square shaped cavity 182. The motor 188 rotates drive shaft 180 which, in turn, rotates valve element 186 causing the pumping of calibration liquid through tube 71. In this manner, the combination of motor 188, drive shaft 180 and valve element 186 perform the function of rotary driving element 101, noted previously, to obtain proper calibration of the sensors in sensor cassette 13. Thus, in this embodiment, valve element 186 functions both to prevent the flow of calibration liquid 16 through tube 71 and as a component of the pumping mechanism to pump the calibration liquid through this tube.

Although an exemplary embodiment of the invention has been shown and described, many changes, modifications and substitutions may be made by one having ordinary skill in the art without necessarily departing from the spirit and scope of this invention.

What is claimed is:

1. An apparatus comprising:
    a housing having an inlet, an outlet, and a passage extending through said housing between said inlet and said outlet;
    a curved wall surface on said housing;
    a tube compressor;
    a compressible tube carried by said housing and defining at least a portion of said passage, said compressible tube being between said curved wall surface and said tube compressor and being wrapped in a circumferential direction at least part way around said tube compressor;
    said tube compressor being mounted on said housing for movement relative to said curved wall surface to squeeze said compressible tube in a region which moves along said compressible tube to thereby pump fluid in said compressible tube;
    a sensor device having a flow-through passage and including at least one sensor to be calibrated, said flow-through passage being in fluid communication with said passage extending through said housing so as to form an endless loop therewith;
    a calibration liquid located in said endless loop so as to wet said sensor; and
    means for keeping said sensor relatively wet during storage of said apparatus, said means comprising an element carried by said housing for urging said tube compressor to squeeze a zone of said compressible tube sufficiently to prevent said calibration liquid from flowing in said compressible tube across said zone.

2. The apparatus of claim 1 wherein said housing includes at least one indexing surface, said tube compressor defines an opening, a portion of said element is in contact with said at least one indexing surface and another portion of said element is located in said opening.

3. The apparatus of claim 1 wherein said housing includes two spaced apart indexing surfaces, said tube compressor defines an opening, a different portion of said element is in contact with each of said indexing surfaces and another portion of said element is located in said opening.

4. The apparatus of claim 1 wherein said compressible tube includes interior walls and a coating which acts to inhibit said interior walls from fusing together during extended periods of time when said compressible tube is squeezed sufficiently to prevent fluid from flowing in said compressible tube across said zone.

5. The apparatus of claim 1 wherein said element is adapted to be coupled to a drive assembly to move said element and thereby cause said tube compressor to move relative to said curved wall surface to pump fluid in said compressible tube.

6. An apparatus comprising:
   a housing having an inlet, an outlet, and a passage extending through said housing between said inlet and said outlet;
   a curved wall surface on said housing;
   a tube compressor;
   a compressible tube carried by said housing and defining at least a portion of said passage, said compressible tube being between said curved wall surface and said tube compressor and being wrapped in a circumferential direction at least part way around said tube compressor;
   said tube compressor being mounted on said housing for movement relative to said curved wall surface to squeeze said compressible tube in a region which moves along said compressible tube to thereby pump fluid in said compressible tube;
   a sensor device having a flow-through passage and including at least one sensor to be calibrated, said flow-through passage being in fluid communication with said passage extending through said housing so as to form an endless loop therewith;
   a calibration liquid located in said endless loop so as to wet said sensor;
   means for keeping said sensor relatively wet during storage of said apparatus, said means comprising an element for urging said tube compressor to squeeze a zone of said compressible tube sufficiently to prevent said calibration liquid from flowing in said compressible tube across said zone;
   a package base; and
   a package cover attached to said package base and, together with said package base, defining an enclosed space in which said housing, said sensor device, and said means comprising said element are located.

7. The apparatus of claim 6 wherein said package base is made of a polymeric material which is air, water and microorganism impermeable and is able to withstand autoclave sterilization conditions, and said package cover is made of a polymeric material which is air and water permeable, microorganism impermeable and is able to withstand autoclave sterilization conditions.

8. The apparatus of claim 6 wherein said package base is made of a polymeric material selected from the group consisting of polycarbonates and mixtures thereof; and said package cover is made of a polymeric material selected from the group consisting of polyolefins and mixtures thereof.

9. The apparatus of claim 6 wherein said compressible tube includes interior walls and a coating which acts to inhibit said interior walls of said compressible tube from fusing together during extended periods of time when said compressible tube is squeezed sufficiently to prevent fluid from flowing in said compressible tube across said zone.

10. A method for producing a calibration system comprising:
    forming a system comprising a sensor device having a flow-through passage and including at least one sensor to be calibrated, and a housing including a curved wall surface and defining a fluid passage so that said flow-through passage and said fluid passage are parts of an endless loop, a tube compressor, and a compressible tube carried by said housing and defining at least a portion of said fluid passage, said tube compressor being mounted on said housing for movement relative to said curved wall surface to squeeze said compressible tube in a region which moves along said compressible tube to thereby pump fluid in said compressible tube;
    introducing a calibration liquid into said endless loop; and
    maintaining said sensor in a relatively wet condition during storage of said system by placing an element relative to said tube compressor to urge said tube compressor to squeeze said compressible tube sufficiently to prevent said calibration liquid from flowing through said endless loop.

11. The method of claim 10 which further comprises:
    locating said system in a package base made of a polymeric material which is air, water and microorganism impermeable and is able to withstand autoclave sterilization conditions;
    attaching a package cover on said package base to thereby form an enclosed package defining an interior space in which said system is located, said package cover being made of a polymeric material which is air and water permeable, microorganism impermeable and is able to withstand autoclave sterilization conditions; and, thereafter,
    subjecting said enclosed package to effective autoclave sterilization conditions to thereby sterilize said system.

* * * * *